(12) United States Patent
Deimling

(10) Patent No.: US 8,436,612 B2
(45) Date of Patent: May 7, 2013

(54) MAGNETIC RESONANCE APPARATUS AND METHOD FOR IMPLEMENTING A NEUROLOGICAL SEQUENCE PROTOCOL

(75) Inventor: Michael Deimling, Moehrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 382 days.

(21) Appl. No.: 12/751,031

(22) Filed: Mar. 31, 2010

(65) Prior Publication Data

US 2010/0244832 A1    Sep. 30, 2010

(30) Foreign Application Priority Data

Mar. 31, 2009    (DE) .................. 10 2009 015 783

(51) Int. Cl.
*G01V 3/00*    (2006.01)
(52) U.S. Cl.
USPC ............................................... 324/307
(58) Field of Classification Search ........... 324/300–322
See application file for complete search history.

(56) References Cited

U.S. PATENT DOCUMENTS

| | | | |
|---|---|---|---|
| 5,814,991 A | 9/1998 | Deimling | |
| 7,254,437 B2 * | 8/2007 | Miyazaki | 600/410 |
| 7,340,290 B2 | 3/2008 | Deimling | |
| 8,131,338 B2 * | 3/2012 | Kassai et al. | 600/410 |

OTHER PUBLICATIONS

"Computer-Aided Detection of Therapy-Induced Leukoencephalopathy in Pediatric Acute Lymphoblastic Leukemia Patients Treated with Intravenous High-Dose Methotrexate," Glass et al, Magnetic Resonance Imaging, vol. 24 (2006) pp. 785-791.
"Assessment of Cerebral Gliomas by a New Dark Fluid Sequence, High Intensity REduction (HIRE): A Preliminary Study," Essig et al, Journal of Magnetic Resonance Imaging, vol. 11 (2000) pp. 506-517.
"HIRE (High Intensity REduction) a New Dark Fluid Sequence," Deimling et al, ISMRM (1996) p. 557.

* cited by examiner

*Primary Examiner* — Dixomara Vargas
(74) *Attorney, Agent, or Firm* — Schiff Hardin LLP

(57) ABSTRACT

In a method and apparatus to generate MR images of an examination region containing tissue with a first T2 time and tissue with a second, significantly longer T2 time are contained, as series of pulse sequences is employed the following pulse sequences: an overview pulse sequence to generate MR overview images, a T1-weighted pulse sequence to generate T1-weighted MR images and a multiple contrast pulse sequence in which at least two groups of magnetic resonance signals are acquired. A first group of magnetic resonance signals is acquired after excitation of a magnetization in a first time period and at least one second group of magnetic resonance signals is acquired in a second time period after the first time period in which the tissue with the significantly longer T2 time delivers the significant signal contribution. An MR image is calculated based on a pixel-by-pixel difference of the absolute values from the magnetic resonance signals of the first group and the second group.

7 Claims, 4 Drawing Sheets

FIG 4
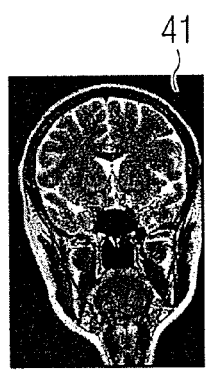
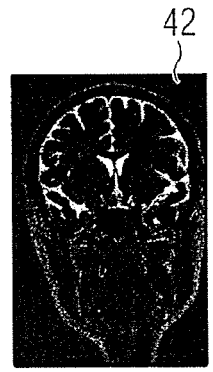
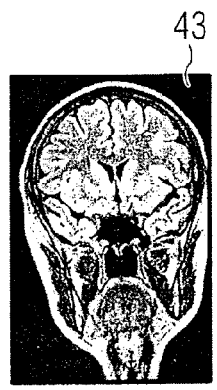
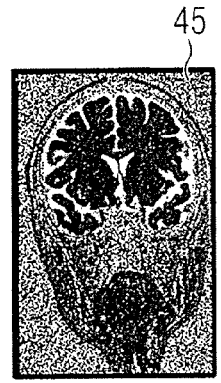

MAGNETIC RESONANCE APPARATUS AND METHOD FOR IMPLEMENTING A NEUROLOGICAL SEQUENCE PROTOCOL

BACKGROUND OF THE INVENTION

1. Field of the Invention

The present invention concerns a method to generate MR images of an examination region in a neurological sequence protocol and a magnetic resonance system for implementing such a method.

2. Description of the Prior Art

In magnetic resonance tomography it is known to acquire multiple pulse sequences to clarify neurological questions in an examination subject. After an overview pulse sequence a T1-weighted pulse sequence is typically used in order to create T1-weighted MR images of a desired region of the examination subject. Furthermore, T2-weighted pulse sequences are acquired to generate T2-weighted MR images. Often to clarify neural questions that pertain to exposures of the brain, the MR signals are acquired so as to exhibit tissue intensity of the cerebrospinal fluid (CSF). White brain matter exhibits a T2 time of approximately 80 ms and grey brain matter exhibits a T2 time of 100 ms, and the cerebrospinal fluid exhibits a T2 time of 2000 ms. In the T2-weighted imaging sequences the high signal of cerebrospinal fluid interferes and marks the other signals so that a diagnosis (for example of multiple sclerosis) is difficult. For this reason the known FLAIR pulse sequence (Fluid Attenuation Inversion Recovery) is typically additionally used. With this imaging sequence with a long inversion time, the magnetization is inverted overall, and the actual imaging is started at a point in time when the longitudinal magnetization of the interfering tissue component is zero. Due to the very long T1 time of the cerebrospinal fluid of approximately 3000 ms, the total acquisition time for this pulse sequence is very long. The examination subject thus must remain for a very long time in the magnetic resonance system. Furthermore, not all questions can be satisfactorily resolved with the FLAIR technique.

From DE 19 616 387 A1 a pulse sequence for a magnetic resonance system is known in which, after an excitation in two time spans at different intervals for excitation, 2 groups of magnetic resonance signals are acquired, with the second group of MR signals being acquired in a time period in which the tissue with a significantly longer T2 time (for example the cerebrospinal fluid) delivers the significant signal contribution. An image is subsequently reconstructed based on the difference of the MR signals of the first and second groups.

The multiple contrast pulse sequence is also known under the name HIRE (High Intensity Reduction Sequence). The interfering high signal of the cerebrospinal fluid is removed via subtraction of the signals of the second group (that were acquired at an echo time of 200 ms, for example) from the MR signals of the first group (with an echo time of 90 ms, for example). However, through this subtraction tissue intensities are also reduced that have T2 values between the values of grey brain matter and white brain matter and the value of the CSF as, for example, is the case for an edema of a tumor or the regions of multiple sclerosis. Moreover, the signal-to-noise ratio is impaired by the subtraction since the noise level is hereby increased by a factor of √2. From DE 101 218 021 it is known to avoid these disadvantages in that the MR signals of the second group are multiplied with a weighting factor, wherein the weighting factor depends on the absolute value [amplitude; magnitude] of the respective signal values of the second group.

SUMMARY OF THE INVENTION

An object of the present invention is to create MR images with which reliable conclusions about neurological illnesses of tissues can be made given an optimally short residence time of the examination subject in the magnetic resonance system.

In a method according to the invention to generate MR images of an examination region containing tissue with a first T2 time and tissue with a second, significantly longer T2 time, a series of pulse sequences is used. The series includes an overview pulse sequence to generate MR overview images and a T1-weighted pulse sequence to generate T1-weighted MR images. The pulse sequence series furthermore includes a multiple contrast pulse sequence in which at least two groups of magnetic resonance signals are acquired, wherein a first group of magnetic resonance signals is acquired after excitation of a magnetization in a first time period and a second group of magnetic resonance signals is acquired in a second time period after the first time period in which the tissue with the significantly longer T2 time delivers the largest signal contribution. Furthermore, an MR image is calculated with a pixel-by-pixel difference of the absolute values of the magnetic resonance signals of the first group and the second group. With this series of overview pulse sequence, the T1-weighted pulse sequence and the multiple contrast pulse sequence, an MR image series with which the question with regard to neurological illnesses can be answered given good signal contrast of the individual MR images can be acquired in as short a time as possible. In particular, it is no longer necessary to acquire a T2-weighted pulse sequence and to subsequently acquire the aforementioned FLAIR pulse sequence; rather, only the multiple contrast pulse sequence must be acquired, such that overall a time gain of multiple minutes per examination subject is achieved. The significance of the MR images acquired with the multiple contrast sequence is likewise greater than given MR images that were acquired with the FLAIR technique.

In forming the difference, the magnetic resonance signals of the second group are advantageously weighted with a weighting factor that depends on the respective absolute value of the pixel of the second group, with the weighting factor being greater given a larger absolute value than given a smaller absolute value. The weighting of the MR signals of the second group advantageously ensues as described in more detail in DE 101 218 021 A1. In addition to the generation of MR images with the weighted difference, with the signals from the multiple pulse sequence it is also possible to calculate an MR image in which the signals of the second group and the signals of the first group are added, with the magnetic resonance signals of the second group in turn being weighted with the weighting factor that depends on the respective absolute value of the pixel of the second group. Furthermore, it is also possible to calculate from the multiple pulse sequence an MR image in which the signal intensity in the MR image essentially corresponds to the T2 time of the tissue that is shown in the respective MR pixel.

The pulse sequence series to acquire MR images with tissue with nerve cells is preferably used in order to be able to identify pathological variations of the nerve cells.

The invention likewise concerns a magnetic resonance system to generate MR images with an image computer and a pulse sequence control unit, wherein the pulse sequence control unit controls the series of pulse sequences as explained above.

BRIEF DESCRIPTION OF THE DRAWINGS

FIG. 4 shows MR images of an examination subject with the different possible contrasts.

DESCRIPTION OF THE PREFERRED EMBODIMENTS

Figure 1:
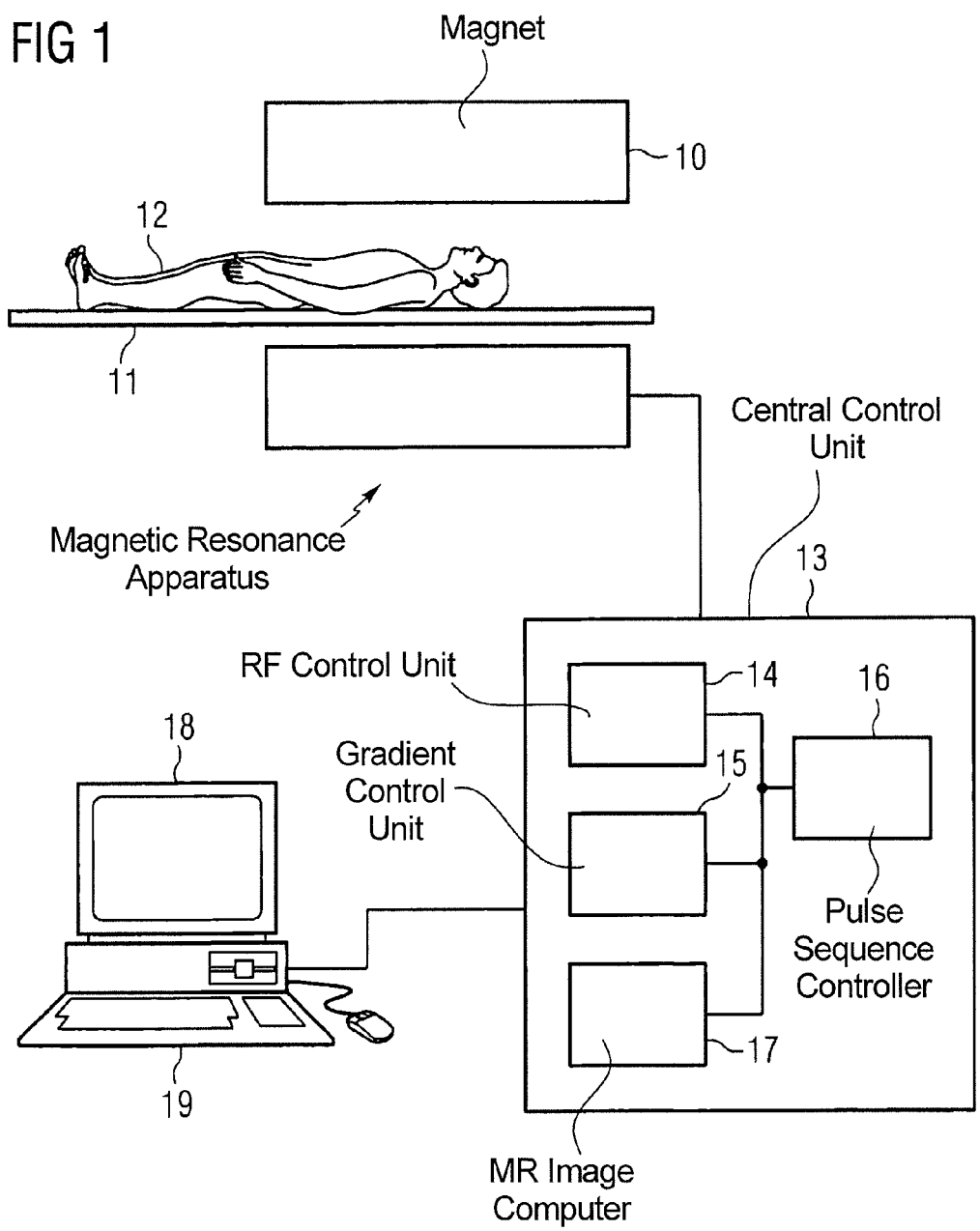
FIG. 1 schematically illustrates an MR system to implement a pulse sequence series for neurological questions.

In FIG. 1 an MR system is shown with which a series of pulse sequences can be executed in a short time span, whereby MR images can be created with which neurological questions can be better clarified. The MR system HAS a magnet 10 to generate a polarization field B0, and an examination subject 12 arranged on a bed 11 is moved into the center of the magnet. The polarization generated by the magnetic field can be deflected by radiation of RF pulse series and switching (activation/deactivation) of magnetic field gradients, and MR signals are induced that can be detected by (for example) acquisition coils (not shown). The mode of operation to generate MR images is known in principle to those skilled in the art, so a detailed explanation of this is not necessary herein. The MR system furthermore has a central control unit 13 that is used to control the MR system. The central control unit 13 has an RF control unit 14, a magnetic field gradient control unit 15 and a pulse sequence controller 16 that controls the sequence of the radiated RF pulses and the switching of the magnetic field gradients depending on the desired image contrast. As is generally known, an MR image computer 17 calculates MR images from the detected MR signals via Fourier transformation and absolute value calculation, which MR images can be displayed on a display unit 18 of the MR system, wherein the MR system can be controlled by an operator via an operating unit 19.

Figure 2:
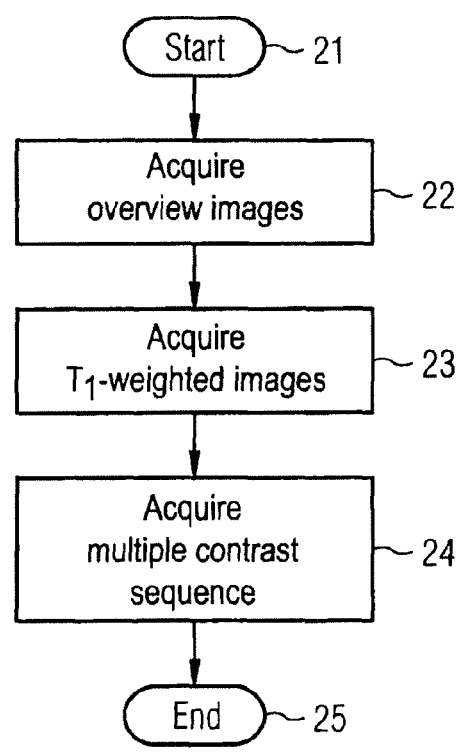
FIG. 2 is a flowchart of a pulse sequence order to clarify neurological questions in accordance with the invention.

The series of pulse sequences that is used in order to clarify neurological questions in examination subject 12 is shown in FIG. 2. After the start of the method in Step 21, in Step 22 overview images (known as localizers) are acquired using which the additional examinations can be planned. In particular, the position of the image planes of the subsequent MR images to be acquired can be planned in the overview images that were acquired with an overview pulse sequence. In an additional Step 23, a T1-weighted pulse sequence is implemented to generate T1-weighted MR images. These T1-weighted MR images are necessary in nearly all questions. In addition to the T1-weighted images, a multiple contrast sequence is implemented in Step 24 in which a series of 180° pulses is radiated after excitation of the magnetization via a 90° pulse. Such a multiple contrast pulse sequence is described more precisely in DE 19 616 387, but the switching of the RF pulses and gradients ensues as described in FIG. 2 herein. After the 90° excitation pulse and the multiple 180° refocusing pulses, the signal echoes generated by the refocusing pulses are acquired in two groups of MR signals: a first group closer to the beginning after excitation of the magnetization and a second group at a time period after the signal readout of the first group. The transverse magnetization responsible for the signals is, for example, relatively high for the grey and white brain matter during the first time period after the acquisition of the first group while the transversal magnetization of the cerebrospinal fluid is lower, corresponding to the smaller available longitudinal magnetization. During the second time period the tissue component of the cerebrospinal fluid is now the signal component with the highest signal proportion. If the signals of the second group are now subtracted from the signals of the first group, overall the signal proportion of the cerebrospinal fluid is significantly reduced. The advantage of this multiple contrast sequence is that a differentiation of white and grey brain matter is markedly better than in the case of the FLAIR sequence with the use of inversion pulses. The method ends in Step 25. As is apparent from FIG. 2, the workflow protocol is shorter than the workflow protocol used in the prior art since—instead of a T2-weighted imaging sequence and the subsequently necessary FLAIR imaging sequence—only the multiple contrast sequence is used, which overall leads to a time savings of approximately 3 minutes per examination subject.

The automatic self-weighting of the MR signals of the second group that is applied in the difference calculation is explained in detail in connection with FIG. 3. The signals of the first group that are acquired by the acquisition coils are sampled, digitized, and the digital values are entered line by line into a raw data matrix and, in Step 31, are subjected to a Fourier transformation in order to obtain absolute values $X_{i,j}$ from the signal values obtained in this way. The absolute value calculation is schematically depicted in Step 32, wherein the image matrix BM1 of the MR signals of the first group is generated. The same Steps are implemented for the MR signals of the second group with two-dimensional Fourier transformation and absolute value calculation, such that an image matrix BM2 with the pixel absolute values $Y_{i,j}$ results. A weighted, pixel-by-pixel subtraction of the second pixel matrix BM2 from the first pixel matrix BM1 can then ensue in the MR image computer 17 so that a complete pixel matrix results as $G_{i,j} = X_{i,j} - f(Y_{i,j}) \cdot Y_{i,j}$. The weighting factor f(y) hereby depends on the absolute value $Y_{i,j}$ of the second image matrix and is described in more detail in DE 10 121 804. The weighting factor depends on the absolute value of the signal of the second group.

Figure 3:
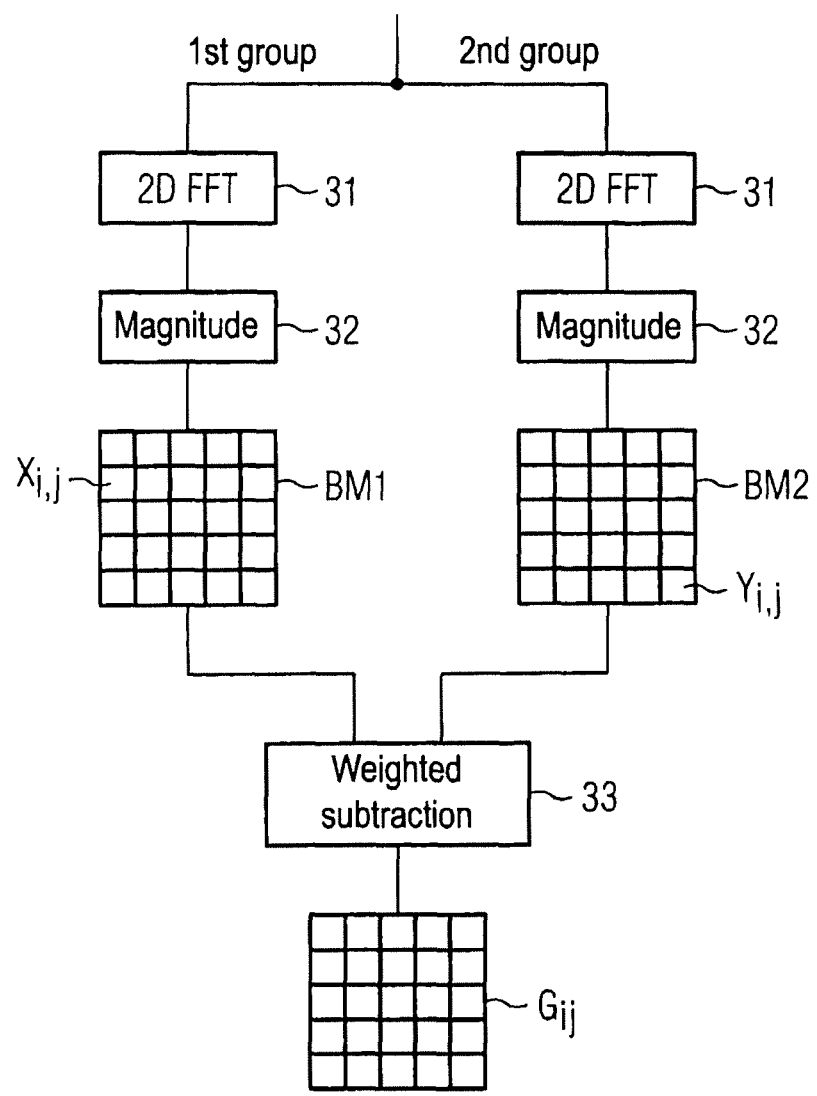
FIG. 3 schematically shows the calculation of the MR images in a multiple contrast sequence of the pulse series.

In FIG. 4 different MR images that were generated from signals of the multiple contrast pulse sequence are shown as examples. The MR image 41 was generated from the MR signals of the first group and shows a standard T2-weighted image of a head in coronary cross section. In the MR image 42 the MR image is shown that was generated from the second group of MR signals with the strong T2 direction. In image 43 the self-weighted subtraction image is shown that was generated with the method from FIG. 3 using the self-weighted weighting factors depending on the absolute value of the MR signals of the second group. In addition to this difference calculation as shown in FIG. 3, the signals of the first group and second group can also be added in a weighted manner in Step 33 instead of a subtraction, whereby an MR image 44 is obtained that exhibits an enhanced 12 contrast. The weighted addition or, respectively, the weighting itself ensues as in the difference calculation and is likewise described in detail in DE 10 121 802 A1. An additional MR image 45 can be calculated from the multiple contrast pulse sequence, namely what is known as a T2 map in which the signal intensities correspond to the T2 times of the shown tissue. Such a T2 map can, for example, be created via the calculation of the difference of the echo times of the MR signals of the first group from the signals of the second group. This echo time difference $\Delta TE$ can now be used to calculate the T2 map:

$$T2 \approx \frac{\Delta TE}{\ln \frac{(X)i,j}{(Y)i,j}}$$

wherein $X_{i,j}$, $Y_{i,j}$ respectively represent the signal values of the first or, respectively, second group, as explained in FIG. 3.

In summary, the described protocol enables the generation of many different MR images with which illnesses of the nervous system can be detected well in a short time period.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to generate magnetic resonance images of an examination region of a subject, said examination region comprising tissue exhibiting a first T2 time and tissue exhibiting a second T2 time that is substantially longer than said first T2 time, said method comprising the steps of:

with a magnetic resonance data acquisition unit in which the examination subject is located, radiating the subject with a series of pulse sequences;

in said series of pulse sequences, initially radiating an overview pulse sequence from which magnetic resonance overview images are generated;

after said overview pulse sequence in said series, radiating a T1-weighted pulse sequence from which T1-weighted magnetic resonance images are generated;

in said series, radiating a multiple contrast pulse sequence in which at least two groups of magnetic resonance signals are acquired, a first of said two groups being acquired after excitation of a magnetization in a first time period and at least a second of said two groups being acquired at a second time period after said first time period, in which said tissue with said substantially longer T2 time produces a dominant signal contribution; and in a processor, calculating a final magnetic resonance image as a pixel-by-pixel difference of respective absolute values of the magnetic resonance signals in said first of said groups and said second of said groups.

2. A method as claimed in claim 1 comprising calculating said difference with the magnetic resonance signals of the second of said groups being weighted with a weighting factor dependent on the respective absolute value of each pixel in the second group, said weighting factor being larger given a larger absolute value than given a smaller absolute value.

3. A method as claimed in claim 1 comprising calculating a further magnetic resonance image in said processor by adding the respective signals acquired from said second of said groups and the signals acquired from said first of said groups in said multiple contrast pulse sequence, with the magnetic resonance signals of said second of said groups being weighted with a weighting factor dependent on respective absolute values of pixels in said second of said groups, said weighting factor being greater given a larger absolute value than given a smaller absolute value.

4. A method as claimed in claim 1 comprising calculating a magnetic resonance image in said processor having a signal intensity therein corresponding to the T2 time of tissue shown in the image, calculated from the multiple contrast pulse sequence.

5. A method as claimed in claim 1 comprising acquiring magnetic resonance images with said series of pulse sequences of nerve cells wherein pathological variations of said nerve cells are depicted.

6. A magnetic resonance apparatus to generate magnetic resonance images of an examination region of a subject, said examination region comprising tissue exhibiting a first T2 time and tissue exhibiting a second T2 time that is substantially longer than said first T2 time, said apparatus comprising:

a magnetic resonance data acquisition unit adapted to receive the examination subject therein;

a control unit configured to operate said data acquisition unit to radiate the subject with a series of pulse sequences, and in said series of pulse sequences, initially radiate an overview pulse sequence from which magnetic resonance overview images are generated, and after said overview pulse sequence in said series, radiate a T1-weighted pulse sequence from which T1-weighted magnetic resonance images are generated, and in said series, radiate a multiple contrast pulse sequence in which at least two groups of magnetic resonance signals are acquired, a first of said two groups being acquired after excitation of a magnetization in a first time period and at least a second of said two groups being acquired at a second time period after said first time period, in which said tissue with said substantially longer T2 time produces a dominant signal contribution; and a processor configured to calculate a final magnetic resonance image as a pixel-by-pixel difference of respective absolute values of the magnetic resonance signals in said first of said groups and said second of said groups.

7. A non-transitory computer-readable storage medium encoded with programming instructions, said storage medium being loaded into a computerized control and processing system of a magnetic resonance apparatus having a magnetic resonance data acquisition unit, and said programming instructions causing said computerized control and processing system to:

operate a magnetic resonance data acquisition unit, in which the examination subject is located, to radiate the subject with a series of pulse sequences;

in said series of pulse sequences, initially radiate an overview pulse sequence from which magnetic resonance overview images are generated;

after said overview pulse sequence in said series, radiate a T1-weighted pulse sequence from which T1-weighted magnetic resonance images are generated;

in said series, radiate a multiple contrast pulse sequence in which at least two groups of magnetic resonance signals are acquired, a first of said two groups being acquired after excitation of a magnetization in a first time period and at least a second of said two groups being acquired at a second time period after said first time period, in which said tissue with said substantially longer T2 time produces a dominant signal contribution; and calculate a final magnetic resonance image as a pixel-by-pixel difference of respective absolute values of the magnetic resonance signals in said first of said groups and said second of said groups.

* * * * *